(12) United States Patent
Harrison et al.

(10) Patent No.: US 9,568,409 B2
(45) Date of Patent: Feb. 14, 2017

(54) VIBRATING WIRE VISCOMETERS

(75) Inventors: Christopher Harrison, Auburndale, MA (US); Matthew T. Sullivan, Westwood, MA (US); Jacques Jundt, Newton, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 437 days.

(21) Appl. No.: 13/353,339

(22) Filed: Jan. 19, 2012

(65) Prior Publication Data
US 2013/0186185 A1 Jul. 25, 2013

(51) Int. Cl.
*G01N 11/16* (2006.01)
*E21B 47/01* (2012.01)
*E21B 49/08* (2006.01)
*E21B 49/10* (2006.01)

(52) U.S. Cl.
CPC ............ *G01N 11/16* (2013.01); *E21B 47/011* (2013.01); *E21B 49/081* (2013.01); *E21B 49/10* (2013.01)

(58) Field of Classification Search
CPC ..................................................... G01N 11/16
USPC .......... 73/54.23, 54.24, 54.25, 54.26, 54.27,73/54.28, 54.29, 54.31, 54.32, 152.18–152.21,73/152.23, 152.29, 152.32, 152.47, 152.55,73/152.58, 54.41
See application file for complete search history.

(56) References Cited

U.S. PATENT DOCUMENTS

| | | | |
|---|---|---|---|
| 7,114,562 B2 | 10/2006 | Fisseler et al. | |
| 7,194,902 B1* | 3/2007 | Goodwin | E21B 49/10 73/152.24 |
| 7,222,671 B2 | 5/2007 | Caudwell et al. | |
| 7,574,898 B2* | 8/2009 | Harrison et al. | 73/54.41 |
| 2001/0045122 A1* | 11/2001 | Ehwald | A61B 5/14532 73/54.23 |
| 2006/0137873 A1* | 6/2006 | Caudwell | G01N 11/16 166/252.5 |
| 2009/0120171 A1* | 5/2009 | Harrison | G01N 11/16 73/64.53 |
| 2010/0006284 A1 | 1/2010 | Sonne et al. | |
| 2011/0023587 A1* | 2/2011 | Madhavan | E21B 47/10 73/54.41 |
| 2011/0030455 A1* | 2/2011 | Matsumoto | G01N 11/16 73/54.41 |

OTHER PUBLICATIONS

Dehestru et al., A microfludic vibrating wire viscometer for operation at high pressure and high temperature, Sciencetific Instrument, vol. 82, published online Mar. 17, 2011—http://www.researchgate.net/publication/50985877_A_microfluidic_vibrating_wire_viscometer_for_operation_at_high_pressure_and_high_temperature.*
G. Dehestru, et al., "A microfluidic vibrating wire viscometer for operation at high pressure and high temperature," Review of Scientific Instruments, vol. 82, 035113 (2011), Mar. 17, 2011.
International Search Report for the equivalent PCT patent application No. PCT/US2013/022328 issued on Jun. 20, 2013.

* cited by examiner

*Primary Examiner* — Michael A Lyons
*Assistant Examiner* — Hoang Nguyen
(74) *Attorney, Agent, or Firm* — Trevor G. Grove

(57) ABSTRACT

Vibrating wire viscometers are disclosed herein. An example viscometer includes a housing defining a chamber and a wire holder disposed in the chamber. The wire holder has an elongated, electrically insulating body and a channel extending along a length of the body. A wire is at least partially disposed in the channel and coupled to the wire holder at opposing ends of the wire holder to tension the wire and electrically isolate the wire from the housing.

19 Claims, 8 Drawing Sheets

VIBRATING WIRE VISCOMETERS

FIELD OF THE DISCLOSURE

This disclosure relates generally to viscometers and, more particularly, to vibrating wire viscometers.

BACKGROUND OF THE DISCLOSURE

Wellbores are drilled at well sites to locate and produce hydrocarbons from subterranean formations. Formation fluid is often collected from the formations to evaluate the economic viability of the well sites. A viscosity of a sample fluid may be calculated based on an electromotive force (emf) of a wire vibrating in the sample fluid. Generally, vibrating wire viscometers hold a sample fluid having a volume of at least 1,000 micro-liters.

SUMMARY

This summary is provided to introduce a selection of concepts that are further described below in the detailed description. This summary is not intended to identify key or essential features of the claimed subject matter, nor is it intended as an aid in limiting the scope of the claimed subject matter.

An example viscometer disclosed herein includes a housing defining a chamber and a wire holder disposed in the chamber. The wire holder has an elongated electrically insulating body and a channel extending along a length of the body. A wire is at least partially disposed in the channel and coupled to the wire holder at opposing ends of the wire holder to tension the wire and electrically isolate the wire from the housing.

Another example viscometer disclosed herein includes a wire to vibrate in a fluid sample within the viscometer and a wire holder to tension the wire and to electrically insulate the wire from electrically conductive portions of the viscometer. The viscometer defines a space around the wire to hold the fluid sample. The fluid sample has a volume between about 2 micro-liters and 100 micro-liters.

Another example viscometer disclosed herein includes means for vibrating in a fluid sample within the viscometer and means for holding the means for vibrating to tension the means for vibrating and to electrically insulate the means for vibrating from conductive portions of the viscometer. The viscometer defines a space around the means for vibrating to hold the fluid sample, and the fluid sample has a volume between about 2 micro-liters and 100 micro-liters.

DETAILED DESCRIPTION

Figure 1:
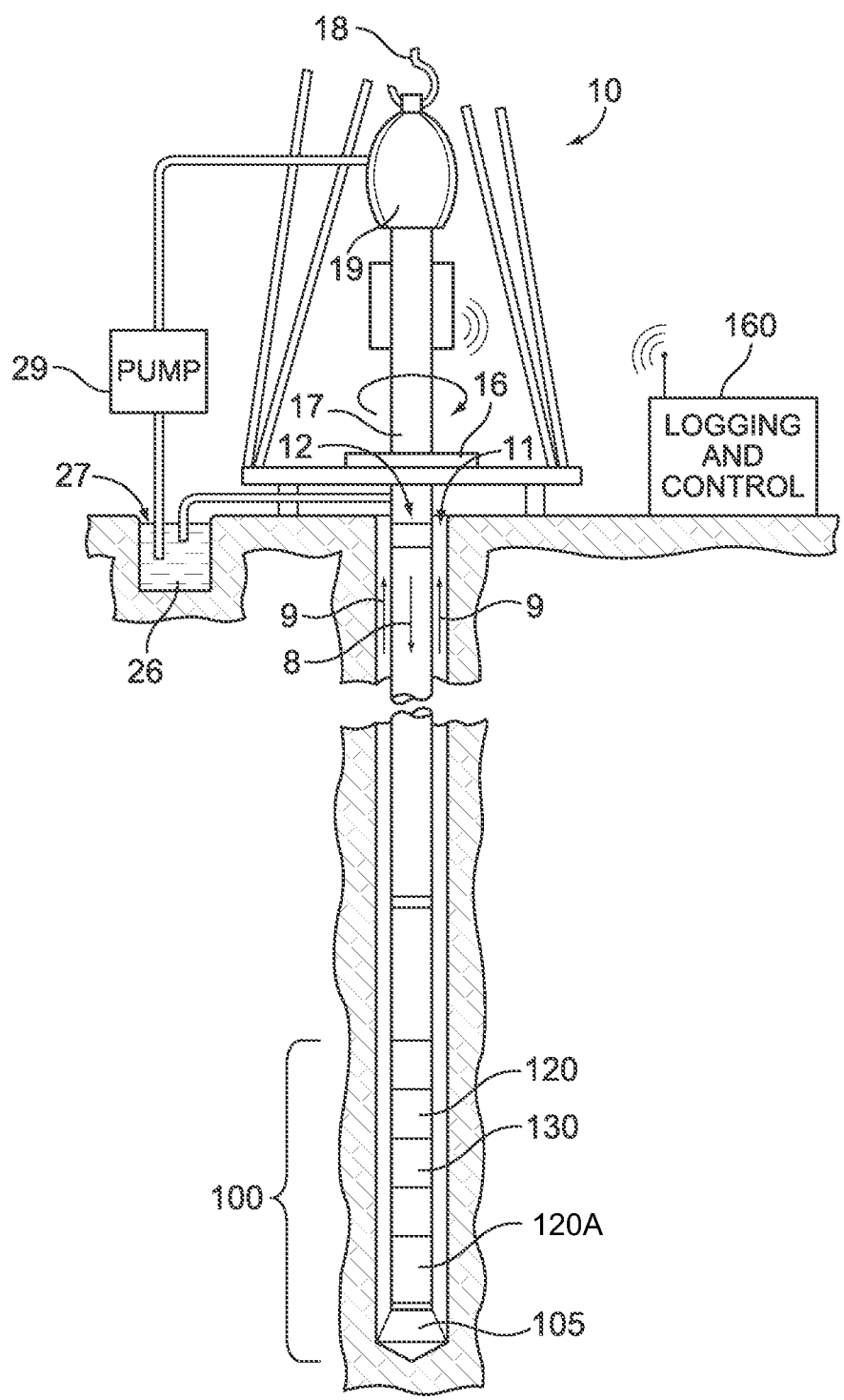
FIG. 1 is a wellsite system according to one or more aspects of the present disclosure.

Different aspects and/or features of example vibrating wire viscometers are disclosed herein. Many of these different aspects and/or features may be combined to realize the respective advantages of these aspects and/or features. Different applications and implementations of the example viscometers disclosed herein may benefit from some combination of the below-described features compared to other combinations.

Wellbores are often drilled to locate and produce hydrocarbons in subterranean formations, and formation fluids are collected to evaluate the economic viability of hydrocarbon reservoirs located in the formations. In some cases, a drilling tool is provided with devices to extract and test formation fluids from formations surrounding the wellbore. In other cases, the drilling tool is removed and a wireline tool is deployed into the wellbore to test and/or sample formation fluids.

Formation fluids are often extracted in a mixture of water, gases, oil, and particulates. Viscosity of the formation fluid is generally a useful parameter to determine appropriate drilling and production methods, which affect the economic viability of the fluid reservoirs. A vibrating wire viscometer may be used to determine viscosity of a fluid. The vibrating wire viscometer includes a conductive wire held under tension and immersed in a sample fluid. The wire is also subjected to a magnetic field. When an electrical current passes through the wire, the magnetic field causes the wire to vibrate, and the viscosity of the formation fluid may be calculated (e.g., based on a voltage generated from a changing magnetic flux through a conductive path including the wire (i.e., an emf of the vibrating wire)).

Dead volume in a vibrating wire viscometer is a volume that collects fluid but which is not in a fluid flow path of the fluid. When a new sample fluid enters the wire viscometer, fluid located in the dead volume may not evacuate the viscometer and, thus, may mix with and contaminate the new sample fluid. Therefore, the viscometer is thoroughly flushed before each viscosity measurement so that the dead volume of the viscometer is at least partially filled with new sample fluid.

In some cases, a few micro-liters of formation fluid may be extracted from a subterranean formation. At the same time, it is often desirable to obtain a viscosity measurement of the oil in the sample fluid mixture. To separate the oil from the mixture, the mixture may be forced through a hydrophobic membrane (e.g., polytetrafluoroethylene (PTFE) membrane). The permeability of the membrane is often very low, and the flow rate of oil through the membrane may equal about one drop (i.e., about 10 micro-liters) per second. However, known wire viscometers, such as those described in U.S. Pat. No. 7,194,902, entitled Apparatus and Method for Formation Evaluation by Hsu, et al. and U.S. Pat. No. 7,222,671, entitled Apparatus and Method for Formation Evaluation by Trusler, et al. generally have internal volumes of at least 1,000 micro-liters. As a result, an interval of time between viscosity measurements may be at least ten to fifteen minutes.

The example viscometers disclosed herein may be microfluidic and may be used to measure a viscosity of a fluid at high temperatures and pressures (e.g., 175° C. and 25,000 psi). An example viscometer disclosed herein defines a space to hold a fluid sample having a volume between about 2 micro-liters and 100 micro-liters. The example viscometer may include a housing defining a chamber, and a wire holder disposed in the chamber. The wire holder may have an elongated, electrically insulating body and a channel extending along a length of the body. The channel may be sized to hold a volume of between about 1 micro-liter and 50 micro-liters of a sample fluid. A wire may be at least partially disposed in the channel and coupled to the wire holder at opposing ends of the wire holder to tension the wire and electronically isolate the wire from the housing. The wire holder may include a groove at each of the ends of the wire holder to substantially center the wire relative to a width of the channel. The housing of the example viscometer may also include electrical connections passing through the housing to electrically connect to the ends of the wire. The electrical connections may include metal pins and insulators to insulate the pins from the housing. Further, a dead volume of the example viscometer may be between about 1 microliter and 50 micro-liters.

Certain examples are shown in the above-identified figures and disclosed in detail below. In describing these examples, like or identical reference numbers are used to identify common or similar elements. The figures may not be to scale and certain features and certain views of the figures may be shown exaggerated in scale or in schematic for clarity and/or conciseness. Accordingly, while the following describes example apparatus, persons of ordinary skill in the art will readily appreciate that the examples are not the only way to implement such apparatus.

While example viscometers are disclosed herein with reference to example downhole tools and wireline tools such as the MDT Modular Formation Dynamics Tester of Schlumberger Ltd., the example viscometers disclosed herein can be used to perform viscosity measurements at other locations. For example, the example viscometers may be used to measure a viscosity of a fluid at a wellsite, in a transportable lab and/or at a fixed-location lab.

FIG. 1 illustrates a wellsite system in which the example viscometer disclosed herein can be employed. The wellsite can be onshore or offshore. In this example system, a borehole 11 is formed in subsurface formations by rotary drilling in a manner that is well known.

A drill string 12 is suspended within the borehole 11 and has a bottom hole assembly 100 which includes a drill bit 105 at its lower end. The surface system includes platform and derrick assembly 10 positioned over the borehole 11, the assembly 10 including a rotary table 16, kelly 17, hook 18 and rotary swivel 19. The drill string 12 is rotated by the rotary table 16, energized by means not shown, which engages the kelly 17 at the upper end of the drill string. The drill string 12 is suspended from a hook 18, attached to a traveling block (also not shown), through the kelly 17 and a rotary swivel 19 which permits rotation of the drill string relative to the hook. As is well known, a top drive system could also be used.

In the example of this embodiment, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105, and then circulates upwardly through the annulus region between the outside of the drill string and the wall of the borehole, as indicated by the directional arrows 9. In this well known manner, the drilling fluid lubricates the drill bit 105 and carries formation cuttings up to the surface as it is returned to the pit 27 for recirculation.

The bottom hole assembly 100 of the illustrated embodiment includes a logging-while-drilling (LWD) module 120, a measuring-while-drilling (MWD) module 130, a rotosteerable system and motor, and drill bit 105.

The LWD module 120 is housed in a special type of drill collar, as is known in the art, and can contain one or a plurality of known types of logging tools. It will also be understood that more than one LWD and/or MWD module can be employed, e.g. as represented at 120A. (References, throughout, to a module at the position of 120 can also mean a module at the position of 120A as well.) The LWD module includes capabilities for measuring, processing, and storing information, as well as for communicating with the surface equipment. In the present embodiment, the LWD module includes a fluid sampling device.

The MWD module 130 is also housed in a special type of drill collar, as is known in the art, and can contain one or more devices for measuring characteristics of the drill string and drill bit. The MWD tool further includes an apparatus (not shown) for generating electrical power to the downhole system. This may include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device, and an inclination measuring device.

Figure 2B:
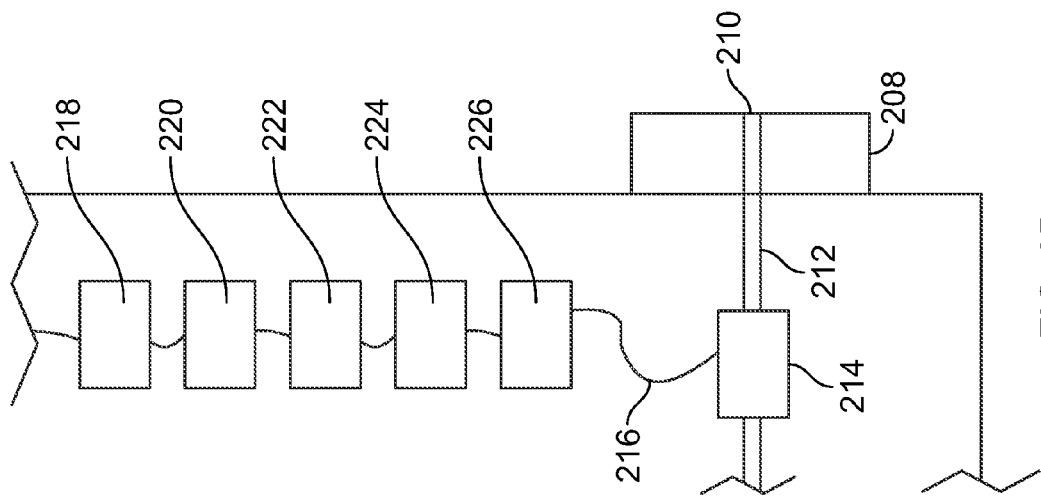
FIG. 2B is a drilling system according to one or more aspects of the present disclosure.
Figure 2A:
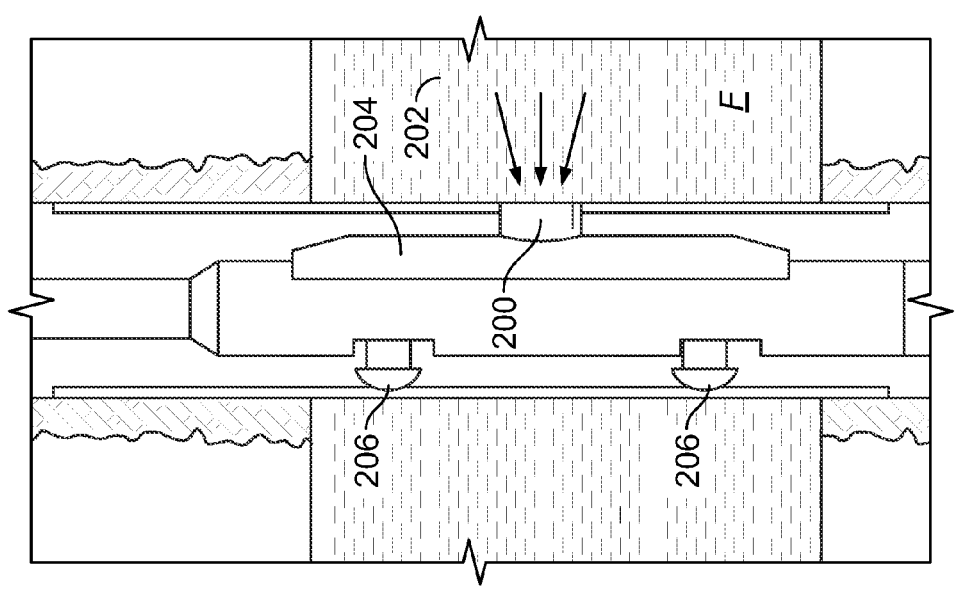
FIG. 2A is a drilling system according to one or more aspects of the present disclosure.

FIG. 2A is a simplified diagram of a sampling-while-drilling logging device of a type described in U.S. Pat. No. 7,114,562, incorporated herein by reference, utilized as the LWD tool 120 or part of an LWD tool suite 120A. The LWD tool 120 is provided with a probe 200 for establishing fluid communication with the formation and drawing the fluid 202 into the tool, as indicated by the arrows. The probe may be positioned in a stabilizer blade 204 of the LWD tool and extended therefrom to engage the borehole wall. The stabilizer blade 204 comprises one or more blades that are in contact with the borehole wall. Fluid drawn into the downhole tool using the probe 200 may be measured to determine, for example, pretest and/or pressure parameters. Additionally, the LWD tool 120 may be provided with devices, such as sample chambers, for collecting fluid samples for retrieval at the surface. Backup pistons 206 may also be provided to assist in applying force to push the drilling tool and/or probe against the borehole wall.

FIG. 2B is a partial cross sectional view of another simplified sample-while-drilling logging device utilized as the LWD tool 120 or part of an LWD tool suite 120A provided with a probe 208. The probe 208 includes an inlet 210 and a main flowline 212 to receive the fluid 202, which may be a mixture of water, gases, and oil. A separation block 214 is positioned near the inlet 210 along the flowline 212. The separation block 214 includes a filter (e.g., a porous fluorinated plastic membrane such as a PTFE membrane) (not shown) to separate the oil and/or particulates from the mixture. Fluid 202 is drawn into the inlet 210 and through the membrane of the separation block 214. Oil separated from the mixture is drawn into a flexible capillary line 216 at a flow rate of, for example, about 1 drop (i.e., about 10 micro-liters) per second. A plurality of sensors 218, 220, 222, 224, and 226 may be placed along the capillary flowline 216 to test and analyze properties of the oil. One of the plurality of sensors 218, 220, 222, 224, and 226 may be an example viscometer disclosed herein.

Figure 3:
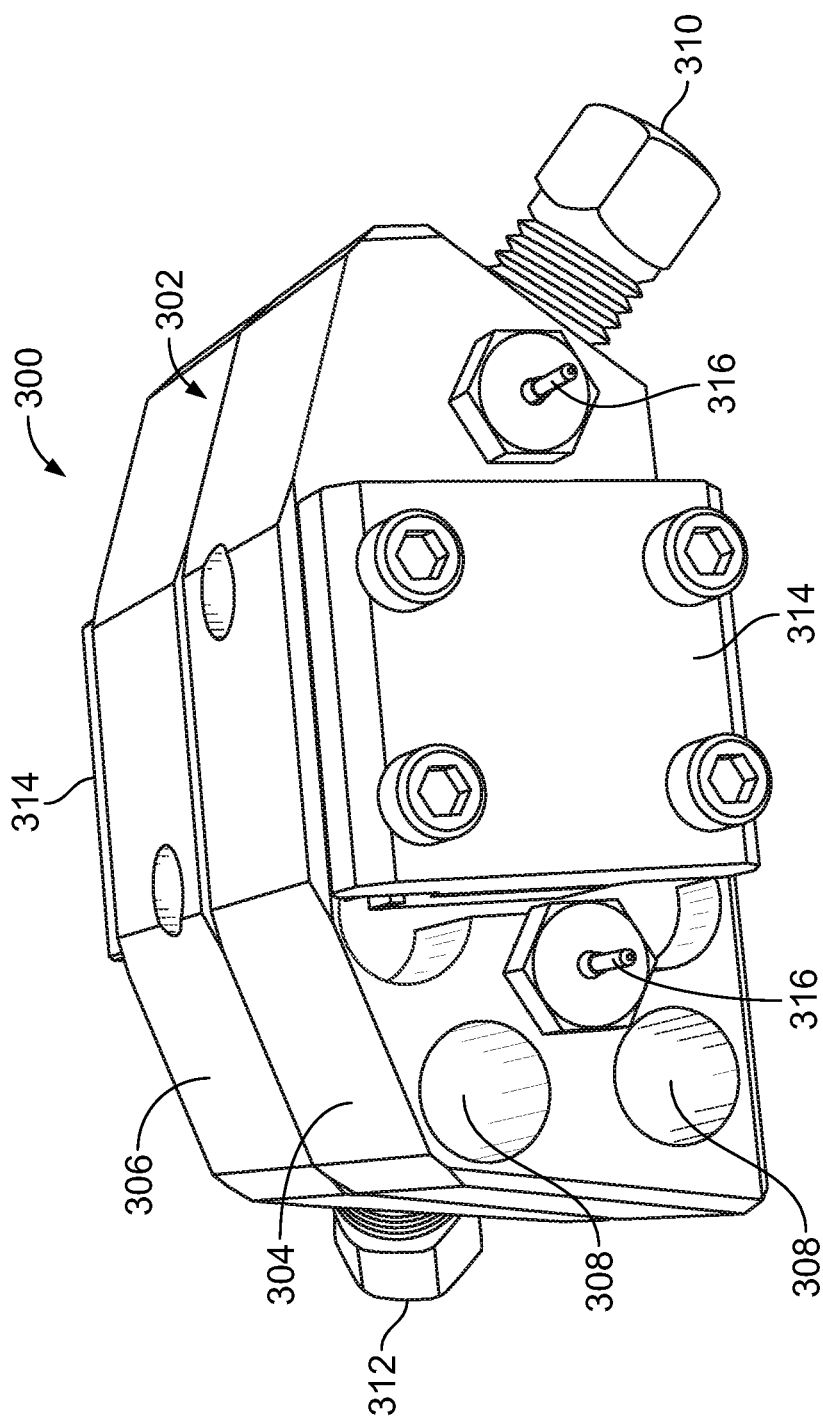
FIG. 3 depicts apparatus according to one or more aspects of the present disclosure.

FIG. 3 depicts an example viscometer 300 disclosed herein. The example viscometer 300 includes a housing 302 defining a chamber 600 (FIG. 6) to hold a fluid sample having a volume of between about 2 micro-liters and 100 micro-liters. The housing 302 may include a first portion 304 and a second portion 306 and may be fabricated with apertures or cutouts 308 to decrease a weight of the example viscometer 300. Sample fluid enters the example viscometer 300 though an inlet 310 of the first portion 304 and exits through an outlet 312 of the second portion 306. Plates 314 are fastened to opposing sides of the housing 302 to secure magnets 602 (FIG. 6) to the housing 302. As discussed in greater detail below, electrical connections 316 pass through the housing 302 to electrically connect to ends of a wire 402 (FIG. 4) disposed in the chamber defined by the housing 302.

Figure 4:
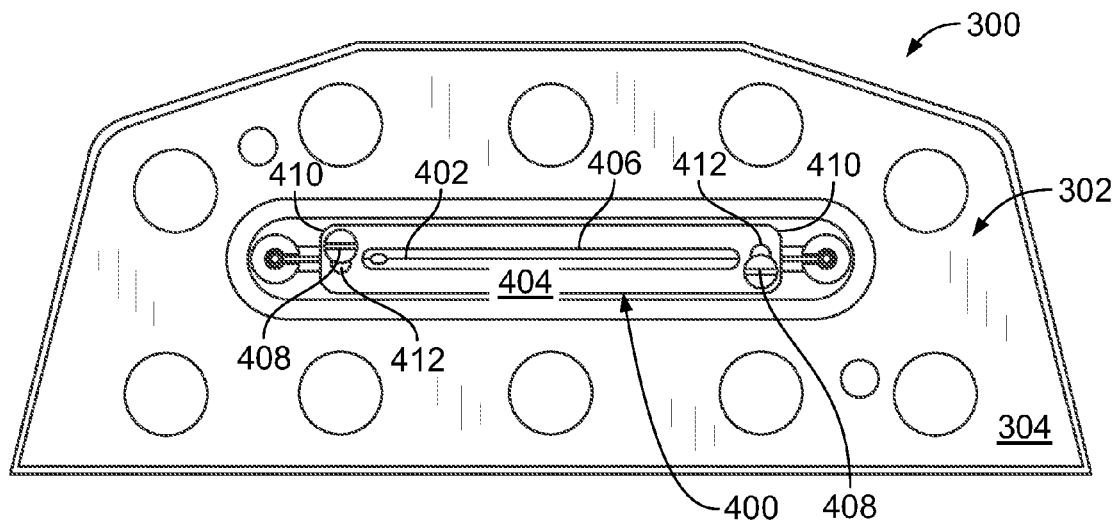
FIG. 4 depicts apparatus according to one or more aspects of the present disclosure.

FIG. 4 depicts the example viscometer 300 with the second portion 306 of the housing 302 removed. As shown in FIG. 4, the example viscometer 300 includes a wire holder 400 to tension the wire 402 and electrically insulate the wire 402 from electrically conductive portions of the viscometer (e.g., the housing 302). The wire holder 400 has an elongated, electrically insulating body 404, which may at least partially be made out of a nonconductive, ceramic material such as silicon nitride. In some examples, at least a portion of the body 404 is glass. In the illustrated example, a width of the body 404 of the wire holder 400 is about 3 millimeters. The above-noted dimension is merely one example and, thus, other dimensions may be used without departing from the scope of this disclosure.

The wire holder 400 also includes a channel 406 extending along a length of the body 404 of the wire holder 400. The channel 406 is open toward the second portion 306 (not shown) of the housing 302. In the illustrated example, the channel 406 is 20 millimeters long, 0.5 millimeters wide, and 0.5 millimeters deep. Thus, the channel 406 may hold a sample fluid having a volume of about 1 micro-liter, which may be substantially equal to or greater than the dead volume of the example viscometer 300. The above-noted dimensions are merely one example and, thus, other dimensions may be used without departing from the scope of this disclosure. In some examples, the channel 406 holds a sample fluid having a volume of about 1 micro-liter. In the example viscometer 300 shown in FIG. 4, the channel 406 is confined within the body 404 of the wire holder 400. However, as described in greater detail below, other example wire holders disclosed herein may have a channel 406 extending through the entire length of the body 404. The wire holder 400 is coupled to the first portion 304 of the housing 302 with screws 408 at each end 410 of the wire holder 400. The wire holder 400 may be coupled to the first portion 304 of the housing with nails, tacks, glue, adhesive, and/or any other suitable fasteners.

The wire 402 is at least partially disposed in the channel 406 and coupled to the wire holder 400 at the opposing ends 410 of the wire holder 400 to tension the wire 402 and electrically isolate the wire 402 from the housing 302. The wire 402 is coupled to the wire holder 400 such that the wire 402 resonates when an electrical current is passed through the wire 402. The wire 402 may be made of tungsten, platinum, Hastelloy™ alloy, Inconel™ alloy, and/or any other suitable conductive material. In some examples, the wire 402 has a coefficient of thermal expansion substantially equal to the coefficient of thermal expansion of the wire holder 400. The wire 402 may have a diameter of about 75 µm. The above-noted dimension is merely one example and, thus, other dimensions may be used without departing from the scope of this disclosure. In the example viscometer 300 shown in FIG. 4, the wire 402 extends through the channel 406 and through the ends 410 of the wire holder 400 via apertures (not shown) on each end 410 of the wire holder 400. The wire 402 is substantially centered relative to a width of the channel 406. The wire 402 in the example viscometer 300 shown in FIG. 4 is vacuum brazed to the wire holder 400 in cavities 412 extending into the apertures on each end 410 of the wire holder 400. In some examples, the wire 402 is coupled to the wire holder 400 via glass sealing, wire bonding, soldering, press fitting, and/or any other suitable coupling. As described in greater detail below, in some example wire holders, the wire 402 is laser welded to the wire holder 400.

Figure 5:
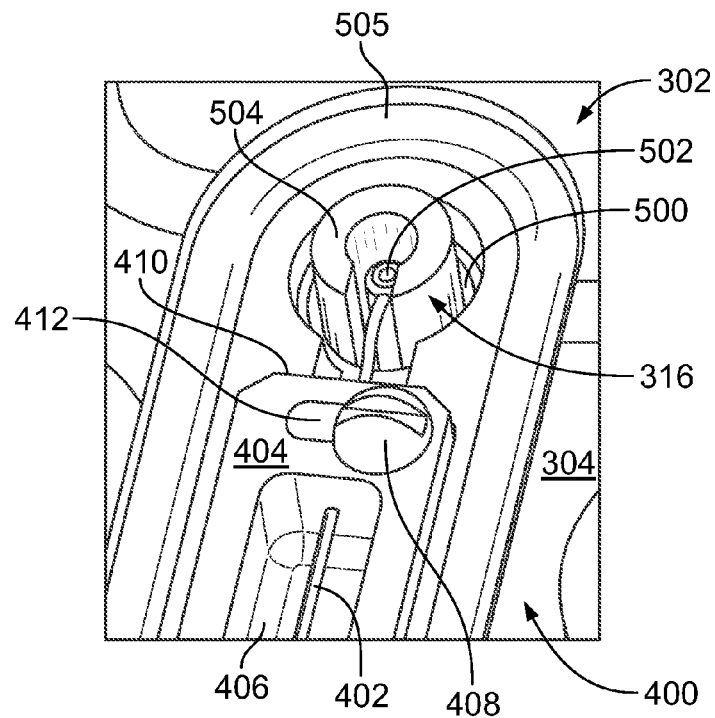
FIG. 5 depicts apparatus according to one or more aspects of the present disclosure.

FIG. 5 depicts an enlarged view of one end 410 of the wire holder 400 of FIG. 4. The ends of the wire 402 are electrically connected to the electrical connections 316 passing through apertures 500 extending through the housing 302. Each electrical connection 316 includes a metal pin 502. The diameter of each pin 502 may be about 1 millimeter. The above-noted dimensions are merely one example and, thus, other dimensions may be used without departing from the scope of this disclosure. Insulators 504 at least partially surround the electrical connections 316 to center the pins 502 in the apertures 500 and insulate the pins 502 from the housing 302. The insulators 504 are made of nonconductive material such as, for example, plastic, glass, a ceramic material, and/or any other suitable material. O-rings (not shown) are compressed between the pins 502 and the first portion 304 of the housing 302 to provide a fluid seal between the pins 502 and the first portion 304 of the housing 302. The electrical connections 316 may be coupled to electronics (e.g., a signal generator, sensor, an analytical circuit, etc.) (not shown). An O-ring 505 is disposed between the first portion 304 and the second portion 306 (not shown) of the housing to form a fluid seal between the first portion 304 and the second portion 306.

Figure 6:
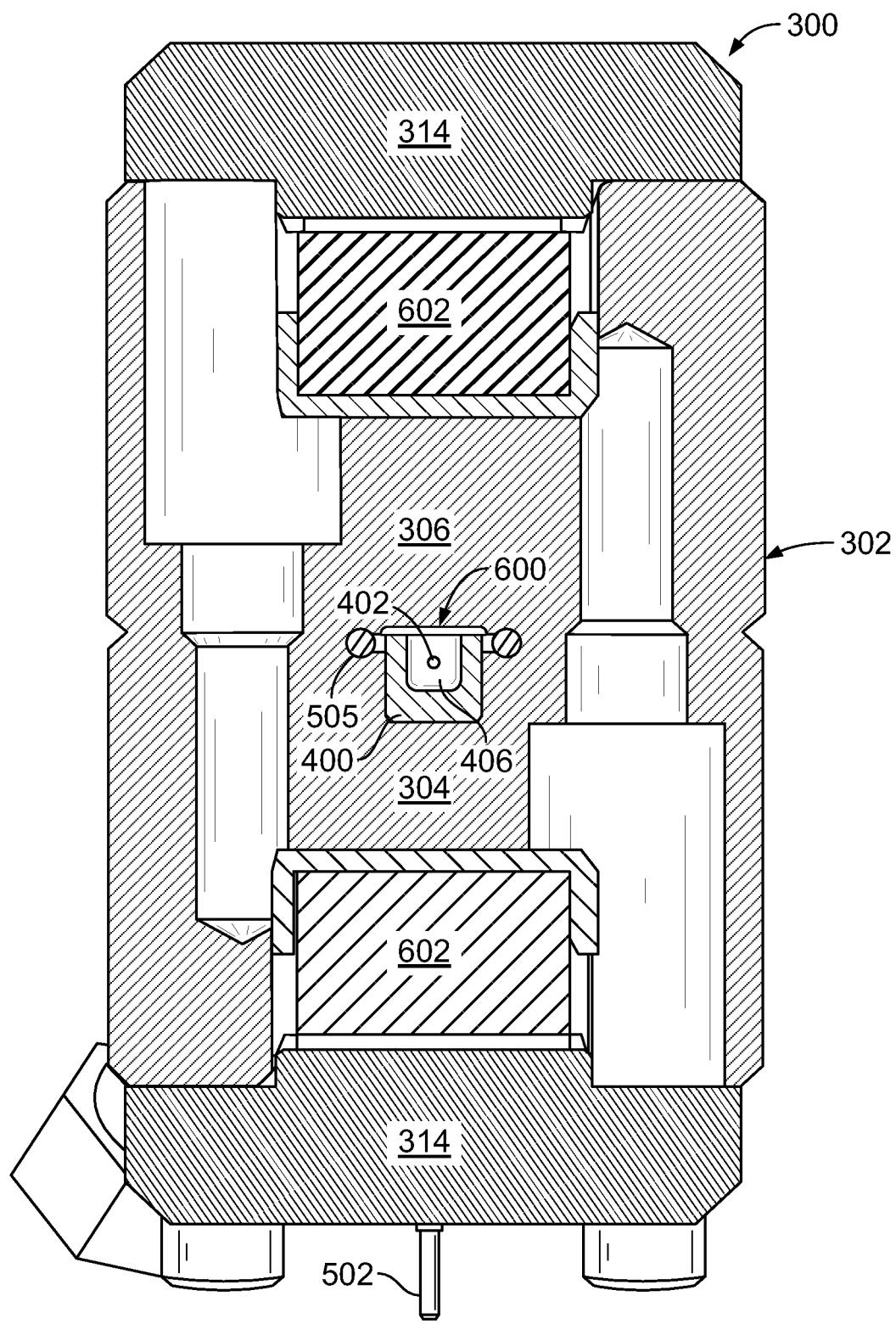
FIG. 6 depicts apparatus according to one or more aspects of the present disclosure.

FIG. 6 depicts a simplified cross-sectional view of a fully assembled example viscometer 300 disclosed herein. As shown in FIG. 6, the housing 302 defines a space or chamber 600 between the first portion 304 and the second portion 306. The chamber 600 holds a sample fluid having a volume of between 2 micro-liters and 100 micro-liters. The wire holder 400, the wire 402 and portions of the electrical connections 316 are disposed in the chamber 600. When the chamber 600 is filled with fluid, the fluid fills the channel 406, covers the wire holder 400 and the portions of the electrical connections 316 disposed in the chamber 600, and immerses the wire 402. The channel 406 of the wire holder 400 is sized to hold a volume of between 1 micro-liter and 50 micro-liters. The body 404 of the wire holder 400 and the insulators 504 substantially fill the chamber 600 to reduce a dead volume of the chamber 600. As a result, the dead volume of example viscometers disclosed herein is between about 1 micro-liter and 50 micro-liters. The O-ring 505 defines a length and a width of the chamber 600.

The first portion 304 and the second portion 306 of the housing 302 are coupled together via fittings (not shown) to define the chamber 600. Magnets (e.g., samarium cobalt magnets) 602 are coupled to the first portion 304 and second portion 306 of the housing 302 below and above the wire 402, respectively, in the orientation of FIG. 6 to provide a magnetic field around the wire 402. The magnets 602 are coupled to the housing 302 via the plates 314. As described in greater detail below, the magnetic field provided by the magnets 602 causes the wire 402 to vibrate when an electrical current runs through the wire 402.

Figure 7A:
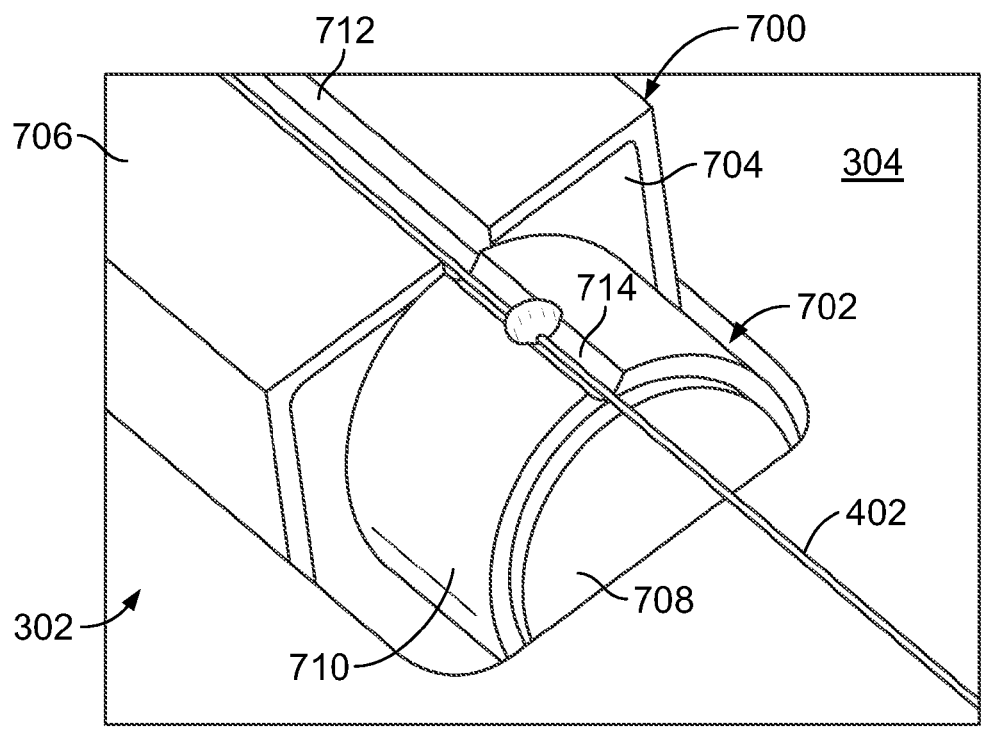
FIGS. 7A and 7B depict apparatus according to one or more aspects of the present disclosure.
Figure 7B:
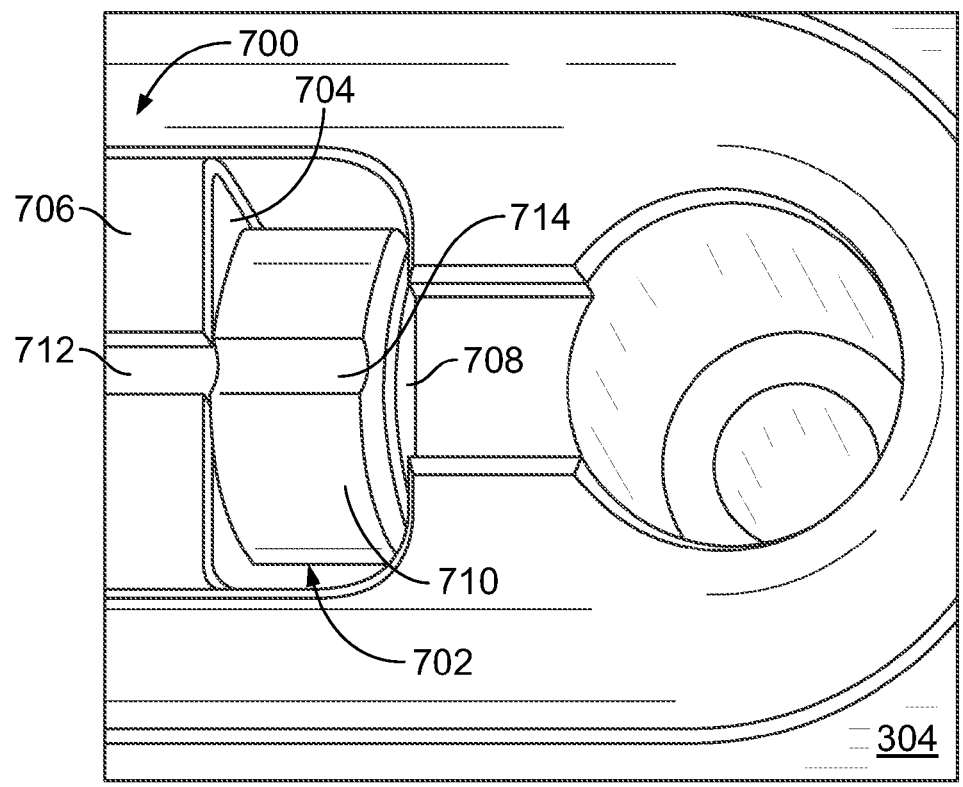

FIGS. 7A and 7B depict another example wire holder 700. The example wire holder 700 depicted in FIGS. 7A and 7B includes a body 706 having wire mounts 702 disposed on opposing ends 704 of the body 706. In the illustrated example, the wire mounts 702 include an electrically insulating post 708 extending laterally from the ends 704 of the wire holder 700. The posts 708 may be coupled to the body 706 or the posts 708 and the body 706 may be integrally formed. A ring 710 is disposed around and coupled (e.g., press fit) to each post 708. In the illustrated example, the rings 710 are metal (e.g., stainless steel), and the wire 402 is tensioned and then laser welded to the rings 710 to fix the wire 402 in a tensioned condition. In some examples, a portion of the body 706 is metal and the posts 708 and/or the rings 710 are a nonconductive material such as, for example, glass, ceramic, and/or any other suitable material. The rings 710 do not contact the housing 302, and the wire 402 extends from the rings 710 to the electrical connections 316, which are electrically insulated from the housing 302 by the insulators 504 (not shown). As a result, the wire 402 is electrically insulated from conductive portions of the housing 302 via the wire holder 700. The wire holder 700 includes a channel 712 extending along a length of the body 706. As shown in FIGS. 7A and 7B, the rings 710 include a semi-circle shaped or V-shaped groove 714 to substantially center the wire 402 relative to the width of the channel 712.

Figure 8:
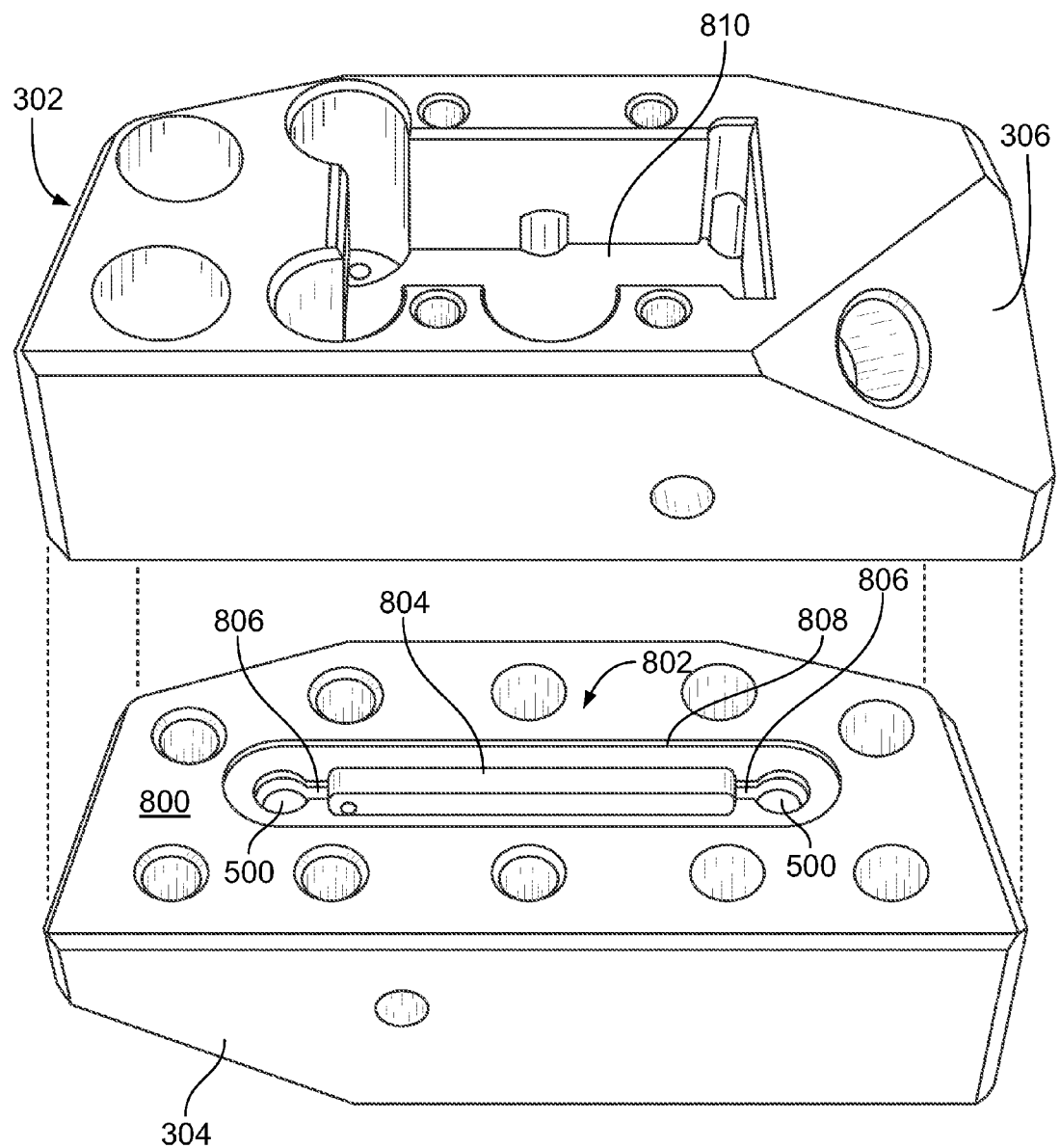
FIG. 8 depicts apparatus according to one or more aspects of the present disclosure.

FIG. 8 depicts an exploded view of the housing 302 of the example viscometer 300. A face 800 of the first portion 304 facing the second portion 306 includes a recess 802 to define part of the chamber 600. The recess 802 includes a containment portion 804 to contain the wire holder 400. The containment portion 804 of the recess 802 is shaped and sized to substantially correspond to the shape and size of the wire holder 400. The recess 802 also includes groove portions 806 to prevent the wire 402 from contacting the housing 302. A first end of each groove portion 806 is adjacent to the containment portion 804, and a second end of each groove portion 806 is adjacent to the apertures 500 extending through the housing 302. The perimeter of the recess 802 includes a sealing portion 808 to retain the O-ring 505. The second portion 306 includes a cavity 810 to receive a magnet (not shown). The first portion 304 also includes a cavity (not shown) to receive a magnet (not shown).

A viscosity of a sample fluid may be calculated by measuring time dependence of amplitudes of the vibrating wire 402 immersed in the sample fluid. For example, after the chamber 600 is filled with the sample fluid, a sinusoidal bust of current having a frequency substantially equal to the resonant frequency of the wire 402 may be run through the wire 402 in the presence of the magnetic field provided by the magnets 602 to vibrate the wire 402. The burst may, for example, last ten resonance periods. A ring-down amplitude generated by the emf of the vibrating wire 402 may be measured by the electronics coupled to the electrical connections 316.

Figure 9:
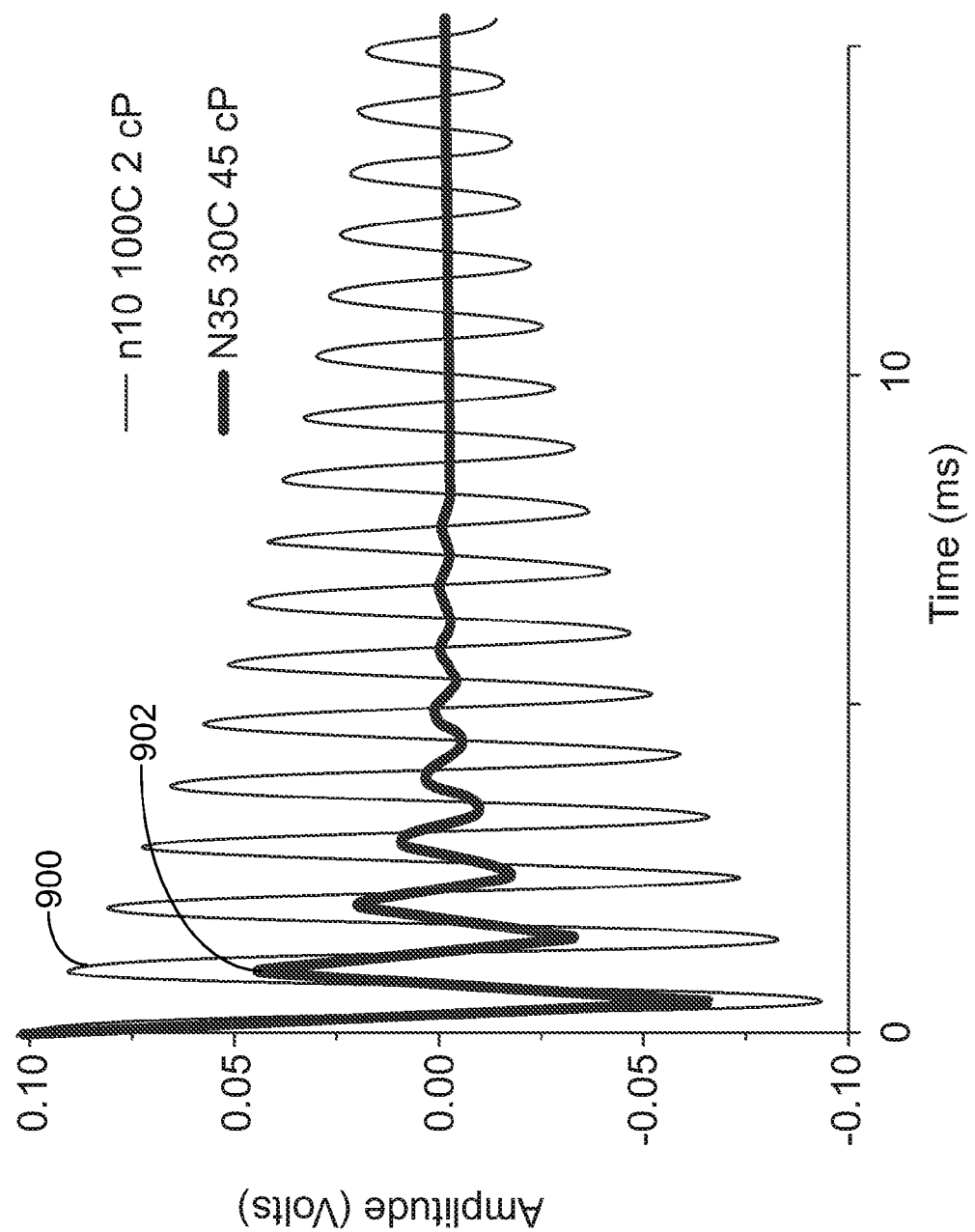
FIG. 9 is a graph illustrating one or more aspects of the present disclosure.

FIG. 9 depicts a graph illustrating example ring-down amplitudes of a wire 402 immersed in a fluid having a viscosity of 2 cP and a fluid having a viscosity of 45 cP as indicated by reference labels 900 and 902, respectively. As shown in FIG. 9, the sample fluids dampen the vibration of the wire 402, and the decrement of the ring-down amplitude is affected by the viscosity of the sample fluid. For example, the greater the viscosity of the sample fluid, the sooner the wire 402 will come to rest after being excited by a burst of current.

After vibrating the wire 402 in a sample fluid, the decrement $\Delta$ and the frequency f of the wire 402 may be determined using Equation 1 below:

$$V(t) = V_0 e^{-\Delta \omega t} \sin(\omega t + \phi),  \quad \text{Equation 1:}$$

where $V(t)$ is a measured ring-down voltage, $V_0$ is the initial voltage of the transient, t is time, $\omega$ is the angular resonant frequency ($\omega = 2\pi f$, where f is the resonant frequency) in Hertz, and $\phi$ is an unknown phase angle. Based on a density $\rho$ of the sample fluid obtained via prior knowledge; a measured radius R of the wire 402; and a decrement $\Delta_0$ and frequency of the wire 402 obtained from a representative ring-down of the wire 402 in air or in a vacuum, the viscosity $\eta$ of a sample fluid may be determined or calculated using Equations 2-6 below:

$$\Delta = \frac{(\rho/\rho_s)k' + 2\Delta_0}{2[1 + (\rho/\rho_s)k]}, \quad \text{Equation 2}$$

where $\rho_s$ is a density of the wire 402 (e.g., 19.3 g/cc for a tungsten wire), $$k = -1 + 2\Im(A), \quad \text{Equation 3:}$$

$$k' = 2\Re(A) + 2\Delta\Im(A), \quad \text{Equation 4:}$$

where $\Re(A)$ and $\Im(A)$ are real and imaginary parts, respectively, of a complex quantity A expressed by $$A = (i - \Delta)\left[1 + \frac{2K_1[\{(i-\Delta)\Omega\}^{1/2}]}{[(i-\Delta)\Omega]^{1/2} K_0[\{(i-\Delta)\Omega\}^{1/2}]}\right], \quad \text{Equation 5}$$

where $K_0$ and $K_1$ are modified Bessel functions, and $\Omega$ is a modified Reynolds number given by $$\Omega = \frac{\omega \rho R^2}{\eta}. \quad \text{Equation 6}$$

Viscosity calculations based on the emf of the vibrating wire 402 in the example viscometers 300 disclosed herein do not use corrections to account for drag induced by the channel 406 (i.e., confinement effects). Walls of an enclosure induce drag on fluid interacting with the walls of the enclosure. Therefore, a viscosity calculation based on emfs of a vibrating wire 402 near walls of an enclosure theoretically results in a large error. As a result, corrections accounting for drag may be used to calculate an accurate viscosity measurement. In the example viscometers 300 disclosed herein, the ratio of the width of the channel 406 to the diameter of the wire 402 is small (e.g., 6.67), and the viscosity calculation described above should theoretically result in a large error without corrections accounting for confinement effects. However, without making any corrections for confinement effects, viscosities of sample fluids may, for example, be calculated within 10 percent of reference viscosity values using the example viscometers disclosed herein.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A viscometer, comprising:
a housing defining a chamber;
a wire holder disposed in the chamber, the wire holder having an elongated electrically insulating body and a grooved channel on an outer surface of the body extending along a length of the body;
a wire at least partially disposed in the grooved channel and directly coupled to the wire holder at opposing ends of the wire holder to tension the wire and electrically isolate the wire from the housing; and
electrical connections passing through the housing to electrically connect to the ends of the wire, the electrical connections being partially disposed in the chamber.

2. The viscometer of claim 1, wherein the grooved channel is sized to hold a volume of between about 1 micro-liter and 50 micro-liters of a sample fluid.

3. The viscometer of claim 2, wherein a dead volume within the viscometer is between about 1 micro-liter and 50 micro-liters.

4. The viscometer of claim 1, wherein the wire holder includes a groove at each of the ends of the wire holder, the grooves to substantially center the wire relative to a width of the grooved channel.

5. The viscometer of claim 4, wherein the wire is fixed to the wire holder via welding, brazing or press fitting adjacent the ends of the wire holder.

6. The viscometer of claim 1, wherein the wire holder comprises a ceramic material.

7. The viscometer of claim 1, wherein the body includes a grooved mount at each end of the body.

8. The viscometer of claim 7, wherein the grooved mounts electrically insulate the wire from the housing.

9. The viscometer of claim 1, wherein the electrical connections include metal pins and insulators to electrically insulate the pins from the housing.

10. A viscometer, comprising:
a wire to vibrate in a fluid sample within the viscometer; and
a wire holder to tension the wire that is directly coupled to the wire holder and to electrically insulate the wire from electrically conductive portions of the viscometer, the wire holder including an elongated body and a grooved channel on an outer surface of the body extending along a length of the body, the viscometer defining a space in the grooved channel around the wire to hold the fluid sample in the space.

11. The viscometer of claim 10, wherein the grooved channel is sized to hold a volume of between about 1 micro-liter and 50 micro-liters of a sample fluid.

12. The viscometer of claim 10, wherein the wire is at least partially disposed in the grooved channel.

13. The viscometer of claim 10, wherein a dead volume within the viscometer is between about 1 micro-liter and 50 micro-liters.

14. The viscometer of claim 10, wherein the wire holder includes a groove at each of the ends of the wire holder, the grooves to substantially center the wire relative to a width of the grooved channel.

15. The viscometer of claim 14, wherein the wire is fixed to the wire holder via welding, brazing or press fitting adjacent the ends of the wire holder.

16. The viscometer of claim 10, wherein the wire holder comprises a ceramic material.

17. The viscometer of claim 10, wherein the body includes a grooved mount at each end of the body.

18. The viscometer of claim 17, wherein the grooved mounts electrically insulate the wire from a housing.

19. The viscometer of claim 18, wherein the housing includes electrical connections passing through the housing to electrically connect to the ends of the wire, the electrical connections including metal pins and insulators to electrically insulate the pins from the housing.

* * * * *